(12) United States Patent
Zhou et al.

(10) Patent No.: US 8,765,475 B2
(45) Date of Patent: Jul. 1, 2014

(54) COLORIMETRIC ABSORBANCE MEASUREMENT METHOD, APPARATUS AND SYSTEM

(75) Inventors: Lihua Zhou, Shenzhen (CN); Zhihong Wang, Shenzhen (CN); Yanwen Weng, Shenzhen (CN); Feng Li, Shenzhen (CN)

(73) Assignee: Shenzhen Mindray Bio-Medical Eletronics Co., Ltd., Shenzhen (CN)

( * ) Notice: Subject to any disclaimer, the term of this patent is extended or adjusted under 35 U.S.C. 154(b) by 836 days.

(21) Appl. No.: 12/257,301

(22) Filed: Oct. 23, 2008

(65) Prior Publication Data

US 2009/0104710 A1    Apr. 23, 2009

(30) Foreign Application Priority Data

Oct. 23, 2007  (CN) .......................... 2007 1 0166617

(51) Int. Cl.
*G01N 35/00* (2006.01)
*G01N 21/00* (2006.01)
*G01N 21/27* (2006.01)
*G01N 21/75* (2006.01)
*G01N 35/02* (2006.01)

(52) U.S. Cl.
USPC ................. 436/50; 436/47; 436/164; 422/63; 422/64; 422/65

(58) Field of Classification Search
None
See application file for complete search history.

(56) References Cited

U.S. PATENT DOCUMENTS 3,819,271 A   6/1974   Beug et al.
4,285,594 A   8/1981   Butts et al.
4,477,190 A   10/1984  Liston et al.
4,908,320 A   3/1990   Zakowski et al.
7,113,282 B2  9/2006   Aguirre et al.
2003/0044990 A1  3/2003  Seto
2003/0072680 A1  4/2003  Higuchi et al.

FOREIGN PATENT DOCUMENTS

| CN | 1409102    A  | 4/2003  |
|---|---|---|
| CN | 2651746    Y  | 10/2004 |
| CN | 1624484       | 6/2005  |
| CN | 2807259    Y  | 8/2006  |
| CN | 1963527       | 5/2007  |
| CN | 101059506     | 10/2007 |
| CN | 101140224  A  | 3/2008  |
| EP | 0289789    A1 | 11/1988 |
| EP | 0316766       | 5/1989  |
| JP | 55-114955  A  | 9/1980  |

(Continued)

OTHER PUBLICATIONS

International Search Report for Chinese Patent Application No. 200710166617.0.

(Continued)

*Primary Examiner* — Neil N Turk
(74) *Attorney, Agent, or Firm* — Kory D. Christensen; Stoel Rives LLP (57) ABSTRACT

Various embodiments disclose a colorimetric absorbance measurement method and a system for performing the same. The method comprises driving a reaction tray carrying a plurality of reaction cuvettes to rotate at a speed; transferring or rotating filters on a filter wheel to a light path of a light beam, starting from a filter of a first wavelength; and sampling photoelectric data when the light beam has passed through each reaction cuvette in some embodiments. The method ensures consistency in the measurement and synchronization between the calibration and the sample test and reliability of the measurements. Various embodiments simplify data processing and reduce the complexity of the system.

14 Claims, 3 Drawing Sheets

(56) References Cited

FOREIGN PATENT DOCUMENTS

| JP | 9297144 | 11/1997 |
|----|---------|---------|
| JP | 11-2566 A | 1/1999 |
| JP | 2007024911 | 2/2007 |

OTHER PUBLICATIONS

English abstract for JP55-114955.
English abstract for JP11-2566.
Xu "Color technical principle and its application to dyeing and finishing (XIV)" State Key Lab of Modem Optical Instrumentation, Zhejiang University, 2006; No. 7, pp. 40-43.
Wang "Technical Issues of the Operation of the Hitachi 260-50 IR Spectrophotometer" 1986, vol. 3, No. 1; 4 pages.
"Development Progress of Clinical Analytical and Diagnostic Bio-Medical Equipment" pp. 39-47.
Chinese Search Report for Chinese Patent Application No. 200710166628.9.
English Abstract for Application No. JP2007024911.
English Abstract for Application No. JP9297144.
English Abstract for Application No. CN1624484.
English Abstract for Application No. CN101059506.
Modern Preventive Medicine, 2006, vol. 33, No. 4, pp. 577-578.
Journal of Natural Science of HeLong Gjiang Unviversity, Apr. 2006, vol. 23, No. 2, pp. 202-205.
Office Action dated Oct. 27, 2011 for U.S. Appl. No. 12/257,323.
Final Office Action dated Apr. 11, 2011 for U.S. Appl. No. 12/257,323.
English Abstract for Application No. CN 1963527.

COLORIMETRIC ABSORBANCE MEASUREMENT METHOD, APPARATUS AND SYSTEM

CROSS-REFERENCE TO RELATED APPLICATIONS

This application claims the benefit under Title 35, United States Code, §119(a)-(d) or §365(b) from Chinese Patent Application No. 200710166617.0, which was filed on Oct. 23, 2007 and is entitled "Colorimetric Absorbance Measurement Method, Apparatus and System", the disclosure of which is incorporated by reference in its entirety.

This application is cross-related to the U.S. patent application under Ser. No. 12/257,323 which is entitled "APPARATUS AND METHOD FOR ANALYZING SAMPLES" and was filed on Oct. 23, 2008. Both applications are assigned to the same assignee—Mindray Medical International Limited, doing business at Mindray Building, Keji 12Road South, High-Tech Industrial Park, Nanshan, Shenzhen, 518057, P. R. China. The content of the aforementioned patent application is incorporated by reference in its entirety into this Application.

FIELD OF INVENTION

Some embodiments relate to a colorimetric absorbance measurement method or process for a biochemical analyzer and an apparatus or an article of manufacture for implementing the same (collectively biochemical analyzer). Some embodiments relate to a colorimetric absorbance measurement system for a biochemical analyzer. Some embodiments relate to an absorbance measurement method and apparatus adapted for a small-sized biochemical analyzer.

BACKGROUND

The biochemical analyzer is a commonly used instrument for clinical diagnosis, which determines various biochemical data, such as hemoglobin, cholesterol, and creatinine, by analyzing serum and/or other body fluids. The biochemical analyzer takes the measurements based on the Lambert-Beer's law which measures how much of the incident light of a certain wavelength range is absorbed by a solution, i.e., absorbance of that solution, to finally determine its concentration upon various calculations.

The monochromatic light used in the measurements may be obtained by means of various monochromators, for example, a diffraction grating or prism, or an interference filter.

Typically, the grating may not be applicable to a small-sized biochemical analyzer because it may be expensive and thus makes it difficult to reduce the size of the instrument due to the use of the grating. The interference filter may be classified into an interference filter operated in a static mode and/or an interference filter operated in a dynamic mode.

In a static mode, each filter corresponds to one of the monochromatic measuring channels, and each has its own photoelectric processing unit. The plurality of channels takes measurements simultaneously. Although the static mode is advantageous in term of speed, the advantages are often compromised due to the higher cost, and thus the interference filter working at the static mode may not be applicable to small-sized or reduced-sized biochemical analyzers.

In a dynamic mode monochromators typically comprise filters arranged in a wheel structure. In a system that employs a monochromator having the filters arranged in a wheel pattern, each monochromatic light path shares a photoelectric sampling and processing system and may thus reduce the cost and gaining popularity in small-sized or reduced-sized biochemical systems and other photometric colorimetric systems. The filter wheel structure may also be implemented in various manners. For examples, the filters may have their surfaces either perpendicular to or parallel with the central axis about which the wheel rotates. The parallel configuration may be less widely adopted in the optical systems because it tends to occupy a larger space, and the measurement accuracy may be adversely affected by the angle of the incident light beams. Hence, the perpendicular configuration is more widely used in the art.

For small- or reduced-sized, automatic biochemical analyzers, it may be even more difficult to obtain a precise, reliable, efficient while simple measurement. Hence, due consideration should be given to whether the analyzer supports a dual-wavelength measurement because the dual-wavelength measurement may be applicable to various test items and may efficiently remove some interferences and thus make a significant contribution to a reliable and efficient measurement.

Currently, some of the small- or reduced-sized automatic biochemical analyzers use filter wheels as their monochromatic light splitting elements. Specifically, a reaction tray rotates in a uniform manner for each cycle, and transfers a constant number of reaction cuvettes sequentially to a photoelectric measurement position. When the reaction tray halts at a certain position, the filter wheel causes a filter that allows a light of a certain wavelength which is specific to the solution in the reaction cuvette to halt at the photoelectric measurement position, and measures the colorimetric absorbance with respect to the light components of that wavelength. Although this method may guarantee the consistency of the measurements, its implementation is rather complicated as it requires halting a corresponding filter at the photoelectric measurement position based on the wavelength that is specific to the solution in each of the reaction cuvette. When the measurement with respect to the current reaction cuvettes is completed, the next reaction cuvette will be transferred or rotated to the measuring position. In these systems, no measurement may be taken until or unless the reaction cuvettes and the filter come to a halt.

Moreover, each time when a reaction cuvette halts and/or restarts, it results in some vibration. This may explain why no data are generally sampled until a period of time lapses such that the vibration may be reduced to a certain extent to avoid unreliable measurement results. Similarly, each time when the filter wheel rotates to a desired wavelength or halts, data are generally sampled when a certain period of time lapses such that the vibration may be reduced to an allowable level. As a result, a much longer time period may be needed for measuring the solutions in the reaction cuvettes. What may further worsen the situation is that, in the case of a dual-wavelength measurement, each time when a reaction cuvette halls the filter wheel may be required to completely halt at filters of two wavelengths to sample data so even a longer time period may be demanded. Additionally, because a different number of reaction cuvettes may demand the dual-wavelength measurement for each cycle, this may result in non-uniform time intervals between sampling points which may be disadvantageous in terms of repeatability and reliability of the measurements. As is hereinabove described, such a method may require transferring a plurality of reaction cuvettes, one by one, to the optical axis for photoelectric data measurement. In order to save time and to ensure uniform time intervals between sampling points, the implementation may be concerned with performing a dual-wavelength measurement on the first and last reaction cuvettes only. In other words, in the cases where data concerning the intermediate procedures are to he sampled, the filter wheel structure as characterized above may not support the dual-wavelength test.

The US patent application publication US 2003/072680 develops a photoelectric measuring method different from those that have been described above. In that application, the filter wheel rotates uniformly and measurements are taken when the reaction tray halts. In this way, that approach effectively removes the unfavorable effects on the measurement due to vibration caused by the start and/or stop of the filter wheel. Meanwhile, because the filter wheel may be in a uniform rotation, when a reaction cuvette stops, it may be allowable to complete absorbance measurements at all wavelengths within a relatively short period of time.

Thus, any test item may be subjected to a dual-wavelength measurement. On the other hand, this patent application publication also discloses that like the other existing techniques, data can also be sampled only when the vibration caused by the start or stop of the reaction tray fades away. Thus, a huge amount of time is similarly demanded for sampling data for each solution in the reaction cuvettes.

In addition, according to the patent application publication, the reaction tray rotates in a fixed manner during each cycle, and the number of cuvettes transferred to the measuring position in each cycle is equal to the total number of the reaction cuvettes in one cycle plus one or minus one. Thus, the reaction tray traverses in a clockwise or counterclockwise direction and stops at a next cuvette position every cycle. The photoelectric sampling is performed on a fixed number of continuous reaction cuvettes every cycle. The longest reaction time (i.e., the time required for continuous monitoring the same item) supported by the instrument directly depends on the number of the reaction cuvettes involved in the photoelectric sampling every cycle and the length of the working cycle.

For example, if the working cycle of the instrument is 20 seconds, and a total of 24 reaction cuvettes are involved in the measurements, then the longest continuous monitoring time period supported by the instrument will be 20*24=480 seconds, i.e., 8 minutes. However, the working cycle of the instrument is directly associated with the measurement speed so this time period should not be unduly long. In the case of a clinic test, the allowable longest continuous monitoring time period may be about 10 minutes in general. Apparently, the measurement speed as described in the aforementioned patent application publication has not been improved enough to address the needs of clinic tests.

SUMMARY

To address the aforementioned disadvantages existing in the prior art, some embodiments provide an absorbance measurement method and apparatus in a small- or reduced-sized, automatic biochemical analyzer that is characterized in that a plurality filters may be arranged in a filter wheel structure. The method may be easily operable in some embodiments. In some embodiments, the method or the apparatus ensures high consistency in the measurement result(s) and thereby enables precise and reliable measurements. In some embodiments, the method or the apparatus may take one or more measurements of all reaction cuvettes at each or at least some of the wavelengths for each or some cycles. In some embodiments, the method or the apparatus may also extract desired data to determine the colorimetric absorbance.

Various embodiments are directed at a method or a process for colorimetric absorbance measurement which comprises the actions of driving a reaction tray carrying a plurality of reaction cuvettes to rotate at a speed, transferring one or more filters which are arranged as or on a filter wheel sequentially to or in a light path, starting from a filter of a first wavelength, and sampling photoelectric data when the light beam has passed through at least one of the plurality of reaction cuvettes. The method may comprise some embodiments wherein the filters arranged as or on the filter wheel are transferred or rotated sequentially to or in the light path at a time interval.

The method or the process may comprise some embodiments wherein when one of the plurality of filters halts on or in the light path, the reaction tray rotates at the speed to transfer at least some of the plurality of the reaction cuvettes on the reaction tray to the light path one by one. The method may comprise some embodiments wherein the filter wheel rotates in a non-measurement state to protect at least one of the one or more filters. The method may comprise some embodiments wherein the act of sampling the photoelectric data is not performed until the speed of the reaction tray is substantially uniform and the filter wheel completely halts.

The method or the process may comprise some embodiments wherein the filter wheel places the filter of the first wavelength on or in the light path at a beginning of a measurement. The method may comprise some embodiments wherein the reaction tray rotates at a substantially uniform speed when the one or more filters are transferred or rotated to the light path one by one, or the reaction tray is configured to be driven to rotate at the substantially uniform speed during a period of time in which a next filter is transferred or rotated to the light path and halts there and stops rotating when the act of sampling photoelectric data is completed.

Some embodiments are directed at an apparatus, a machine, or an article of manufacture to perform the one or more methods or one or more processes as described above.

DETAILED DESCRIPTION

Some embodiments provide a colorimetric absorbance measurement method or process and comprise the actions of: driving a reaction tray carrying a plurality of reaction cuvettes to rotate at a predetermined speed; transferring filters arranged on a filter wheel sequentially to a light path, starting from a filter of a first wavelength; and sampling photoelectric data when the light beam has passed through each reaction cuvette. Some embodiments also describe a corresponding apparatus for performing these embodiments of the method.

In some embodiments, the filters arranged on the filter wheel may be sequentially transferred to the light path at a predetermined time interval.

In some embodiments, when one of the filters halts on the light path, the reaction tray rotates at a substantially uniform speed to transfer at least some of the reaction cuvettes on the reaction tray to the light path one by one. One of ordinary skills in the art will clearly understand that various factors such as the variations in the utility or the allowances and/or tolerances in the design and/or manufacturing of the components may cause the rotation speed to fluctuate and the reaction tray thus reaches a substantially uniform rotation speed even though the rotation speed is designed or intended to be uniform.

In some embodiments, the filter wheel rotates in the non-measurement state where no measurement is taken.

In some embodiments, photoelectric data may not be sampled until the reaction tray starts to rotate at a uniform speed and the filter wheel comes to a complete stop.

In some embodiments, the filter wheel places the filter of the first wavelength on the light path at the beginning of the measurement.

In some embodiments, the reaction tray, which is driven by a driving unit, keeps rotating at a uniform speed when the filters are transferred or rotated to the light path one by one, or the reaction tray is driven to rotate at a uniform speed during the period of time in which the next filter is transferred or rotated to the light path and completely halts there, and stops rotating when the measurements are completed.

Some embodiments provide a colorimetric absorbance measurement method or process which comprises: a driving unit for driving a reaction tray carrying a plurality of reaction cuvettes to rotate at a predetermined speed; a turning unit for transferring filters arranged on a filter wheel sequentially to a light path, starting from a filter of a first wavelength; and a conversion unit for sampling photoelectric data when the light beam has passed through each reaction cuvette. Some embodiments also describe the corresponding apparatus for performing the method as described above.

In some embodiments, the turning unit transfers or rotates filters which are arranged on the filter wheel sequentially to the light path at a predetermined time interval.

In some embodiments, every time when one of the filters halts on the light path, the reaction tray is configured to rotate at a uniform speed to transfer or to rotate each of the reaction cuvettes on the reaction tray to the light path one by one.

In some embodiments, the filter wheel rotates in the non-measurement state where no measurement is taken.

In some embodiments, the conversion unit may not sample data until or unless the reaction tray starts to rotate at a uniform speed and the filter wheel comes to a complete stop.

In some embodiments, the filter wheel is configured to place the filter of the first wavelength on the light path at the beginning of the measurement.

In some embodiments, the reaction tray, which may be configured to be driven by a driving unit, keeps rotating at a uniform speed when the filters are transferred or rotated to the light path one by one, or the reaction tray may be configured to be driven to rotate at a uniform speed during the period of time in which the next filter is transferred or rotated to the light path and comes to a complete stop there, and stops rotating when the measurements are completed.

Some embodiments provide a colorimetric absorbance measurement system for a biochemical analyzer which comprises: a light source for emitting a light beam; a lens for converging the light beam; a filter wheel comprising a plurality of filters arranged thereon for selecting wavelengths of the light beam for measurement; a reaction tray for carrying a plurality of reaction cuvettes, wherein at least one of the plurality of reaction cuvettes is used as a colorimetric utensil which holds a sample solution to be measured; a photoelectric detection unit for detecting the light beam having passed through the reaction cuvettes and converting a light signal to an electrical signal; a conversion unit for amplifying and analog-to-digital converting the electrical signal obtained by the photoelectric detection unit; a control unit for controlling a filter wheel driving unit and a reaction disc driving unit at least one of which is configured to cause the filter wheel and the reaction tray to rotate by receiving a signal fed from a motor; and a processor for processing the signal having been amplified and/or converted by the conversion unit. The system as provided is characterized in that the reaction tray rotates in a predetermined speed under the control of the control unit, and the filter wheel sequentially transfers the filters to the light path under the control of the control unit, starting from a first filter of a first wavelength.

The colorimetric absorbance measurement system for a biochemical analyzer according to some embodiments may optionally comprise a sensor which is configured to detect the position of the filter wheel and notifies the control unit so that the filter wheel is configured to cause the filter of the first wavelength to halt in the light path at the beginning of at least some measurements.

In some embodiments of the colorimetric absorbance measurement system for a biochemical analyzer, the filter wheel may also be arranged or configured such that the filters provided thereon are transferred or rotated to or positioned in the light path between the reaction cuvettes and the photoelectric detection unit in order to perform functions comprising selecting the wavelengths of the light beam having passed through the sample solution to be measured. In some embodiments, the filter wheel may also be arranged or configured such that at least one of the filters provided thereon is transferred or rotated to or positioned in the light path behind one of the reaction cuvettes. In these embodiments, the at least one of the filters is transferred to, rotated to, or positioned in the light path between the one of the reaction cuvettes and the photoelectric detection unit to perform functions comprising selecting the wavelengths of the light beam having passed through the sample solution to be measured.

Advantages of the colorimetric absorbance measurement system for a biochemical analyzer utilizing according to the present invention may comprise the following.

The colorimetric absorbance measurement system measures the sample in at least one of the reaction cuvettes at various wavelengths and thereby achieving a high testing efficiency in some embodiments.

No particular limitation is imposed on the longest reaction time and the number of reaction cuvettes so the system according to some embodiments may be widely applicable.

The measurement may be easily implemented in various embodiments.

In some embodiments, the method or the system supports a dual-wavelength measurement for nearly all of test items.

Figure 1:
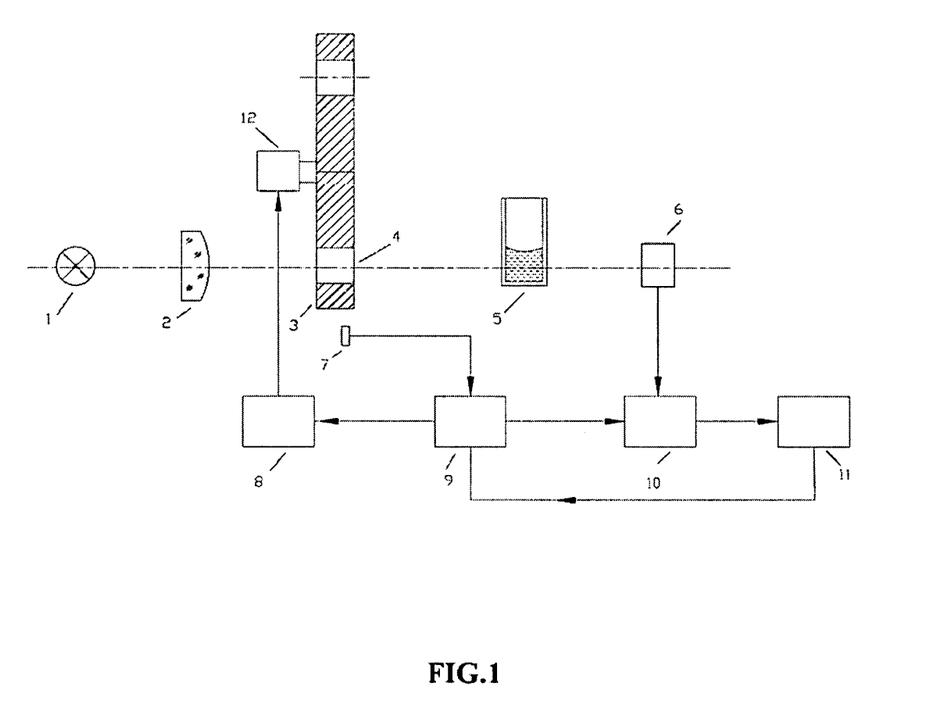
FIG. 1 illustrates a schematic diagram of a light path of a colorimetric absorbance measurement system according to the present invention.

FIG. 1 illustrates a colorimetric absorbance measurement system according to some embodiments. In some embodiments, a compound color light emitted by a tungsten halogen lamp 1 or other light sources serving substantially similar purposes converges when traversing a lens 2, and is then directed to a narrow hand filter 4, where wavelengths are selected The selected monochromatic light is fed into a colorimetric cuvette 5 which holds a solution to be measured and acts as a colorimetric utensil in some embodiments. The light components absorbed by the colorimetric solution may then be converted to one or more electrical signals by the photoelectric detector 6 in some embodiments. The converted one or more electrical signals may then be, for example, amplified or converted by an A/D conversion unit 10 and may finally be transferred or sent to a microprocessor 11 for data processing and calculation in some embodiments.

A plurality of relatively narrow band filters 4 allowing light components of different wavelengths are configured to be arranged on a wheel 3 at regular intervals in some embodiments. In some other embodiments, the filters 4 may also be configured on the wheel 3 at some irregular intervals or spacing. In some embodiments, ten narrow band filters 4 are employed for biochemical analyzers. In these embodiments, eight filters are employed for illustration. The filter wheel 3 may be configured to be driven by a stepping motor 12 or other similar motors, which may be configured to be driven by a drive signal fed from a drive circuit unit 8 in some embodiments. The control circuit 9 may be employed to govern which modes the motor is operated in and when the operation modes may be switched.

In some embodiments when the system is in an idle state, the control circuit 9 is configured to cause the filter wheel 3 to rotate at a substantially uniform and relatively slow pace, while in a measurement mode, the control circuit 9 is configured to cause the filter wheel 3 to be periodically alternated between "rotation" and "halt" states in a fixed manner in some embodiments. When the filter wheel 3 rotates one cycle, the filters therein experience eight "rotations" and eight "halts" in some embodiments. In these embodiments, these eight narrow band filters 4 will be sequentially conveyed to the light path in a predetermined time period for the colorimetric absorbance measurement in some embodiments.

At the time of measurement, the narrow band filter 4 remains still in some embodiments. When the colorimetric absorbance measurement is completed, the motor drives the filter wheel 3 to rotate, and causes another band filter 4 of a second wavelength to stop on the light path, and another measurement at the second wavelength may be performed in some embodiments. The same procedure continues until measurement at each of the 8 wavelengths is taken to finish the entire photoelectric measurement in some embodiments. Thereafter, measurement results of the sample solution at eight wavelengths may be outputted in some embodiments.

In some embodiments, when the measurement begins, the position of the filter in the filter wheel 3 placed on the light path is always regarded as the position of a first narrow band filter of a first wavelength. This position is determined using a sensor 7 in some embodiments. In these embodiments, the sensor 7 senses the position of the filter placed on the light path and feeds back a signal indicative of the sensed filter wheel position to the control circuit 9 which controls the rotation of the filter wheel 3 and transfers or sends the wavelength information to the microprocessor 11 for data processing in some embodiments.

Figure 2:
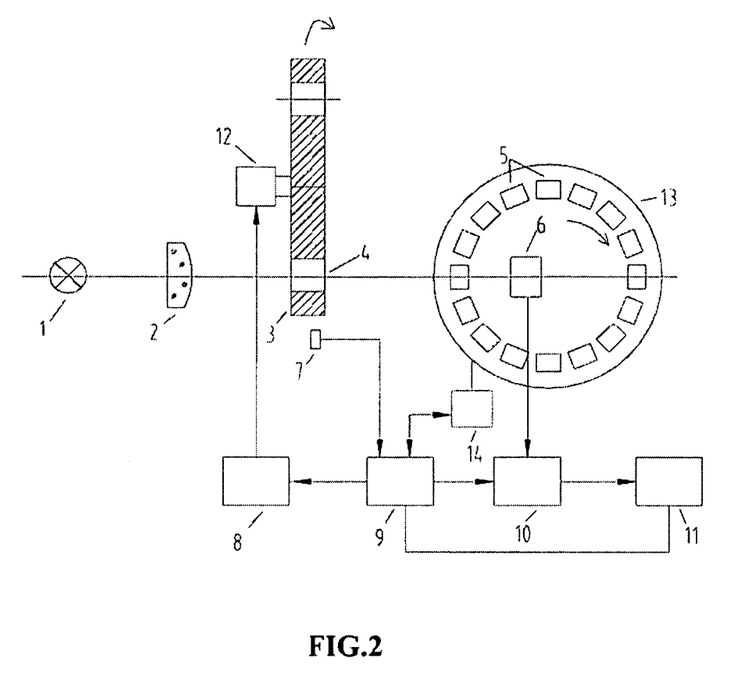
FIG. 2 illustrates a schematic diagram of the light path of the colorimetric absorbance measurement system according to the present invention, viewed from the top.

FIG. 2 shows a top view of the colorimetric absorbance measurement system according to some embodiments. The colorimetric absorbance measurement system comprises a plurality of reaction cuvettes 5, at least one of which allows substantially simultaneous measurement of a plurality of samples. In this example as shown in FIG. 2, 16 reaction cuvettes are employed for illustration. The reaction cuvettes 5 are configured to be carried by a reaction tray 13, which is driven by a reaction tray driving circuit 14 in some embodiments. The driving circuit 14 may he driven by drive signals fed from the control circuit 9. Initially, the control unit 9 is configured to cause the reaction tray 13 to rotate, while sending a halt signal to the filter wheel 3, such that the filter wheel 3 halts at the first wavelength position in some embodiments.

When the filters 4 come to a complete stop, and the reaction tray rotates at a uniform and speed, the control circuit 9 is configured to activate the A/D conversion unit 10 to start, at the first wavelength, measurements of the 16 reaction cuvettes one by one when they are sequentially transferred or rotated to the light path for measurement in some embodiments. When the filters 4 come to a complete stop and exhibit no or some tolerable amount of vibration, and the reaction tray rotates at a uniform speed, the control circuit 9 is configured to activate the A/D conversion unit 10 to start, at the first wavelength, measurements of the 16 reaction cuvettes one by one when they are sequentially transferred or rotated to the light path for measurement in some embodiments.

When the photoelectric measurement is completed for the first wavelength, the filter wheel 3 rotates again and halts the next filter having a second wavelength in the light path in some embodiments. When the filter wheel 3 comes to a complete halt the A/D conversion unit 10 starts measuring the content in the 16 cuvettes at the second wavelength in some embodiments. The above actions are repeated until measurements are taken for the entire 16 reaction cuvettes at each of the wavelengths in some embodiments. Finally, the reaction tray stops rotation in some embodiments. The reaction tray keeps rotating at a uniform speed throughout the measurement procedure in some embodiments. When the measurements are completed, the A/D conversion unit 10 transmits the data to a microprocessor 11 for data processing and calculation.

Figure 3:
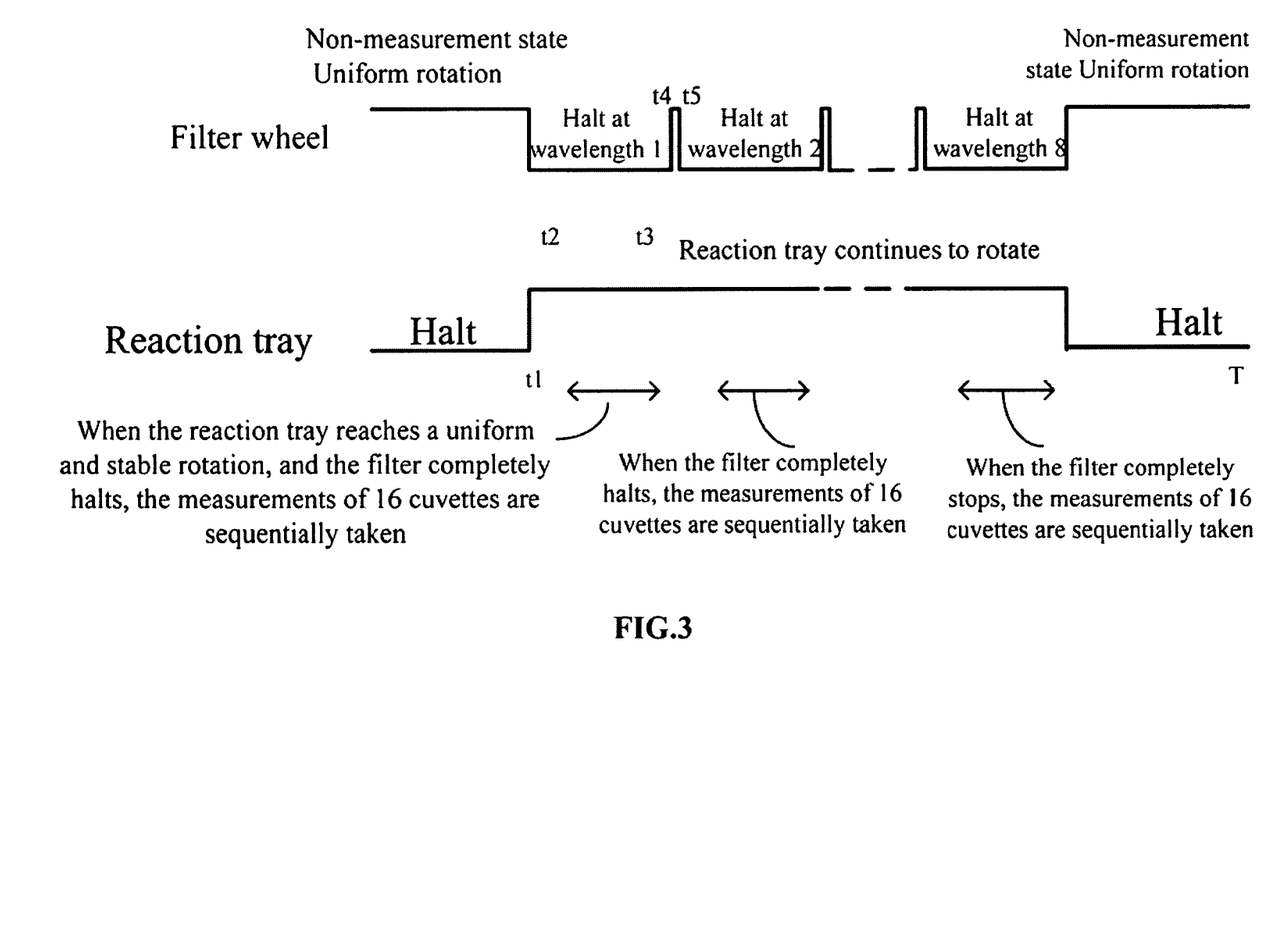
FIG. 3 illustrates a schematic diagram showing the flow of operations of a filter wheel and a reaction tray.

The operations of the above filter wheel and reaction tray are illustrated with reference to the timing sequence diagram of FIG. 3. At the beginning of each cycle T, the reaction tray remains still, and the filter wheel is in a non-measurement state in some embodiments. In some embodiments, the filter wheel rotates in a relatively slow speed when it is in a non-measurement state. In some embodiments, the filter wheel rotates in a relatively slow speed when it is in a non-measurement state so as to prevent issues caused by continuous exposure such as aging of the filter(s) or straining the filter(s) due to continuous exposure. At time t1, the reaction tray speeds up until it rotates at a substantially uniform speed.

One of ordinary skills in the an would clearly understand that the manufacturing and/or operational tolerances or slacks may cause fluctuations in the speed of a mechanism even though the speed of the mechanism is intended or designed to be uniform. At the same time t1, the filter wheel starts rotation and halts the filter of a first wavelength (i.e., wavelength 1) on the light path in some embodiments. At time t2 when the filter wheel 3 comes to a complete stop, and the reaction tray rotates at a substantially uniform speed, measurements of the 16 reaction cuvettes start and are completed at time t3 in some embodiments. At time t4, the filter wheel 3 continues to rotate, and halts the filter with a second wavelength (i.e., wavelength 2) on the light path at time t5 in some embodiments. Measurements of the 16 cuvettes are not started until vibrations totally cease or subdue to be at or below a threshold in some embodiments.

The above steps may be repeated until each of the 8 wavelengths is involved in the measurement in some embodiments. When the photoelectric measurement is completed, the reaction tray speeds down and halts, and the filter wheel rotates at a uniform and slow pace in some embodiments. So far, a measurement cycle T has completed. During the measurement, the filter wheel rotates to place one by one the filters arranged on the wheel at a predetermined, a substantially uniform, or even an irregular or non-uniform time interval on the light path in some embodiments. During the time period which it takes each filter to comes to a complete halt the reaction tray rotates at a relatively higher speed such that all reaction cuvettes are transferred to the measuring position on or in the light path one by one in some embodiments. For one cycle, data with respect to these 8 wavelengths may be obtained for each reaction cuvette in some embodiments.

A substantially identical procedure may be repeated for each photoelectric measurement which makes the control much simpler in some embodiments. Data concerning the eight wavelengths are each obtained in a fixed time period and thus enable a uniform time interval for testing in some embodiments. Moreover, the method according to some embodiments ensures consistency in the measurement and synchronism between the calibration and the sample test and thus renders the measurement more reliable in some embodiments. Finally, since the amount and format of data sampled each time are substantially consistent with one another, the data processing is significantly simplified and the complexity of the system is thus considerably reduced.

In addition to or in the alternative, the same effect of the optical structure of the aforementioned examples may also be achieved by arranging the filter wheel between the reaction cuvette and the photoelectric detector.

During the photoelectric sampling, the reaction tray may stop moving after the measurement for each wavelength is completed in some embodiments. During the time period in which the filter rotates and completely stops the next filter in or on the light path, the reaction tray starts to rotate again and reaches a substantially uniform rotation speed in some embodiments. Since the time period in which the reaction tray accelerates to the uniform speed is typically not longer than the time which the filter wheel takes to rotate the next filter to the light path and completely stops there, the constant alternating between "start" and "stop" of the reaction disc may also achieve the aforementioned function and effect in some embodiments. In some embodiments, the difference between the two comprises the control manner(s).

In the foregoing specification, the invention has been described with reference to specific embodiments thereof. It will, however, be evident that various modifications and changes may be made thereto without departing from the broader spirit and scope of the invention. For example, the above-described process flows are described with reference to a particular ordering of process actions. However, the ordering of many of the described process actions may be changed without affecting the scope or operation of the invention. The specification and drawings are, accordingly, to be regarded in an illustrative rather than restrictive sense.

What is claimed is:

1. A colorimetric absorbance measurement method, comprising:
    emitting a light beam via a light source;
    driving a reaction tray carrying a plurality of reaction cuvettes to rotate at a substantially uniform speed through the light beam;
    transferring one or more filters which are arranged as or on a filter wheel sequentially to or in a light path of the light beam, starting from a filter of a first wavelength;
    halting the filter wheel at one or more time intervals;
    sampling, via a photoelectric detection unit, photoelectric data at the one or more time intervals when the filter wheel is halted and the light beam has passed through at least one of the plurality of reaction cuvettes; and
    controlling, via a controller, the timing of halting the filter wheel and the timing of sampling photoelectric data;
    calculating, via a processor, a colorimetric absorbance using the sampled photoelectric data.

2. The colorimetric absorbance measurement method according to claim 1, wherein transferring the one or more filters comprises transferring the one or more filters arranged as or on the filter wheel sequentially to or in the light path at a time interval, in response to a control signal from the controller.

3. The colorimetric absorbance measurement method according to claim 1, further comprising: the controller signaling the reaction tray to rotate at a speed to transfer at least some of the plurality of the reaction cuvettes on the reaction tray to the light path one by one at one or more time intervals, when one of the one or more filters is halted on or in the light path.

4. The colorimetric absorbance measurement method according to claim 1, wherein at least two filters are arranged as or on the filter wheel, and further comprising:
    the controller causing the reaction tray to be rotated at the substantially uniform speed;
    the controller causing the one or more filters to be transferred sequentially to or in the light path of the light beam while the reaction tray is rotating at the substantially uniform speed; and
    the controller causing each filter to be sequentially transferred to or in the light path of the light beam.

5. A colorimetric absorbance measurement apparatus, comprising:
    a light source to emit a light beam;
    a reaction tray comprising a plurality of reaction cuvettes;
    a driving unit to drive the reaction tray and cause each of the plurality of reaction cuvettes to pass through a light path of the light beam, such that the reaction tray rotates at a substantially uniform speed;
    a turning unit to transfer one or more filters which are arranged as or on a filter wheel sequentially through the light path of the light beam, starting from a filter of a first wavelength;
    a conversion unit to sample photoelectric data at one or more time intervals while the filter wheel is halted and while the reaction tray is rotating at the substantially uniform speed, wherein the light beam is allowed to pass through at least one of the plurality of the reaction cuvettes;
    a controller in communication with the turning unit and the conversion unit, wherein the controller is configured to selectively cause the turning unit to halt the filter wheel, and wherein the controller is configured to cause the conversion unit to selectively sample photoelectric data while the filter wheel is halted; and
    a processor, in communication with conversion unit, to calculate colorimetric absorbance using sampled photoelectric data.

6. The colorimetric absorbance measurement apparatus according to claim 5, wherein the turning unit is configured to transfer or rotate at least one of the one or more filters in or on the light path at a time interval, in response to a control signal from the controller.

7. The colorimetric absorbance measurement apparatus according to claim 5, wherein the reaction tray is configured to rotate at a substantially uniform speed to transfer or rotate at least one of the plurality of reaction cuvettes on the reaction tray to the light path.

8. The colorimetric absorbance measurement apparatus according to claim 5, wherein the controller is configured to selectively cause the filter wheel to rotate at a second speed.

9. The colorimetric absorbance measurement apparatus according to claim 5, wherein the controller is selectively configured to cause the reaction tray to rotate a substantially uniform speed, and
    wherein the controller is configured to cause the conversion unit to selectively sample photoelectric data while the filter wheel is halted and the reaction tray is rotating at a substantially uniform speed.

10. The colorimetric absorbance measurement method of claim 1, in which the controller is configured to signal the conversion unit to sample the photoelectric data within uniform time interval for each of the plurality of reaction cuvettes.

11. The colorimetric absorbance measurement method of claim 1, wherein the filter wheel comprises at least one filter of a second wavelength, and further comprising sampling photoelectric data of at least one of the reaction cuvettes at the first wavelength and at the second wavelength.

12. The colorimetric absorbance measurement apparatus of claim 5, wherein the conversion unit is configured to sample the photoelectric data within a uniform time interval for each of the plurality of reaction cuvettes.

13. The colorimetric absorbance measurement apparatus of claim 5, wherein the filter wheel comprises at least one filter of a second wavelength, and wherein the controller is configured to cause the conversion unit to sample the photoelectric data of at least one of the reaction cuvettes at the first wavelength and the second wavelength.

14. The colorimetric absorbance measurement method of claim 1, further comprising:
   the controller causing the reaction tray to rotate at the substantially uniform speed; and
   the controller causing the photoelectric detection unit to sample the photoelectric data while the reaction tray is rotating at the substantially uniform speed.

\* \* \* \* \*